US011686676B2

(12) United States Patent
Van Wyck et al.

(10) Patent No.: US 11,686,676 B2
(45) Date of Patent: Jun. 27, 2023

(54) IN-SITU NEAR INFRARED SENSOR UNIT AND METHOD OF MAKING THE SAME

(71) Applicant: Landscan, LLC, San Luis Obispo, CA (US)

(72) Inventors: Neal Edward Van Wyck, Jericho, VT (US); Gregory Anderson, San Diego, CA (US); Stephen Farrington, Gaysville, VT (US); Daniel James Rooney, Lake Oswego, OR (US); Woody Guthrie Wallace, Madison, WI (US)

(73) Assignee: LandScan LLC, San Luis Obispo, CA (US)

( * ) Notice: Subject to any disclaimer, the term of this patent is extended or adjusted under 35 U.S.C. 154(b) by 0 days.

(21) Appl. No.: 17/187,833

(22) Filed: Feb. 28, 2021

(65) Prior Publication Data
US 2022/0276160 A1    Sep. 1, 2022

(51) Int. Cl.
*G01N 21/359*    (2014.01)
*G01N 21/03*    (2006.01)
*G01N 21/3563*    (2014.01)

(52) U.S. Cl.
CPC ....... *G01N 21/359* (2013.01); *G01N 21/0303* (2013.01); *G01N 21/3563* (2013.01); *G01N 2021/0389* (2013.01)

(58) Field of Classification Search
CPC ............. G01N 21/359; G01N 21/0303; G01N 21/3563; G01N 2021/0389
See application file for complete search history.

(56) References Cited

U.S. PATENT DOCUMENTS

| 5,739,536 A * | 4/1998 | Bucholtz ................. G01J 3/02 |
| | | 250/253 |
| 6,115,061 A | 9/2000 | Lieberman et al. |
| 9,285,501 B2 | 3/2016 | Christy et al. |
| 10,337,159 B2 | 7/2019 | Morgan et al. |

(Continued)

FOREIGN PATENT DOCUMENTS

DE    102004020350 A1    10/2005
WO    WO-2018094497 A1 *    5/2018    ............ G01J 3/0218

OTHER PUBLICATIONS

Wijewardane et al., VisNIR integrated multi-sensing penetrometer for in situ high-resolution vertical soil sensing, Feb. 15, 2020, Soil & Tillage Research, vol. 99, pp. 1-10. (Year: 2020).*

(Continued)

*Primary Examiner* — Christine S. Kim
(74) *Attorney, Agent, or Firm* — Downs Rachlin Martin PLLC (57) ABSTRACT

An in situ near infrared sensing unit includes a housing allowing the sensing unit to be inserted in a variety of media. A transparent window is formed in the sidewall of the housing. A sensing element is mounted inside the housing. The sensing element is configured to emit near infrared light provided from a light source external to the housing, and the sensing element is configured to collect near infrared light transmitted through the transparent window. A mirror is mounted in the housing at an angle with respect to the transparent window and opposite the sensing element. The angle allows the mirror to reflect the near infrared light, emitted by the sensing element, through the transparent window.

22 Claims, 9 Drawing Sheets

(56) References Cited

U.S. PATENT DOCUMENTS

2011/0106451 A1* 5/2011 Christy .............. G01N 21/8507
702/5
2017/0370064 A1* 12/2017 Morgan ................. G01J 3/108

OTHER PUBLICATIONS

Poggio M., Brown, D., Bricklemyer, R. Laboratory-based evaluation of optical performance for a new soil penetrometer visible and near-infrared (VisNIR) foreoptic, Computers and Electronics in Agriculture, 2015, vol. 115, pp. 12-20, ISSN 0168-1699, https://doi.org/10.1016/j.compag.2015.05.002. Published Online.

Bellon-Maurel, V., McBratney, A, Near-infrared (NIR) and mid-infrared (MIR) spectroscopic techniques for assessing the amount of carbon stock in soils—Critical review and research perspectives, Soil Biology and Biochemistry, 2011, vol. 43, Issue 7, pp. 1398-1410, ISSN 0038-0717, https://doi.org/10.1016/j.soilbio.2011.02.019. Published Online.

Ng, W. et all., Convolutional neural network for simultaneous prediction of several soil properties using visible/near-infrared, mid-infrared, and their combined spectra, Geoderma, 2019 vol. 352, pp. 251-267, ISSN 0016-7061, https://doi.org/10.1016/j.geoderma.2019.06.016. Published Online.

Stenberg, B, et al. Chapter Five—Visible and Near Infrared Spectroscopy in Soil Science, Editor(s): Donald L. Sparks,Advances in Agronomy, Academic Press, 2010, vol. 107, pp. 193-206, ISSN 0065-2113, ISBN 9780123810335, https://doi.org/10.1016/S0065-2113(10)07005-7. Published on-line.

VERTEK Brochure, 2013, Published in USA.

* cited by examiner

IN-SITU NEAR INFRARED SENSOR UNIT AND METHOD OF MAKING THE SAME

BACKGROUND OF THE INVENTION

1. Field of the Invention

The present invention relates to the field of near infrared spectrometry. More specifically, it relates to an in-situ NIR sensor unit, especially for sensing components of soil and other media in which it may be positioned.

2. Description of the Related Art

NIR spectrometry (NIRS) is a reliable testing method utilized by laboratories to determine the constituents of a sample. Test samples are collected in the field, placed in appropriate sample containers and cataloged for future analysis. Once a laboratory receives the samples, each sample container is opened, and a portion of the sample is placed under an NIR sensor machine. The NIR sensor machine uses a light source to illuminate the sample with a broad spectrum of near infrared light such as a wavelength range of 800 to 2500 nm. The sample absorbs light according to different bonds which may be present among the constituents of the sample. A NIR sensor, within the machine, measures the intensity of the light as a function of wavelength before and after the light interacts with the sample. By assessing the change in reflected wavelengths of NIR light, the laboratory may determine the compounds present in the sample.

Areas in which NIRS is particularly useful for sample analysis include soil and/or earth related fields including geology, agriculture, and environmental contamination, etc. However, the requirements to collect samples in the field, transport the samples to a laboratory, and waiting for the laboratory perform the for analysis, introduce inefficiencies related to costs, tracking and time lag in receiving the results.

A VIS-NIR equipped soil penetrometer is disclosed in U.S. Pat. No. 10,337,159 B2 ("U.S. Pat. No. 10,337,159"). This penetrometer provides a housing with a conical tip for insertion into soil. Inside the housing, the VIS-NIR sensing components include a light source separate from a fiber optic sensor and a mirror disposed therebetween. The mirror reflects the light emitted from the light source (i.e., lamp or LED) through a window in the housing to the soil external to the penetrometer. Then, light is reflected by the soil through the transparent window into the housing and absorbed by the fiber optic sensor.

The light source being contained within the housing and/or near the sensors such as in U.S. Pat. No. 10,337,159 has disadvantages. The light source is separate from the fiber optic sensor and positioned closer to the tip of the penetrometer than the light source. In this position, the light source utilizes space that may be used to add additional sensors which would allow for ore accurate NIR sensing. Also, the accuracy of the NIR and any other sensors may be reduced by heat generated by the light source in the area of sample sensing. Moisture content, for example, is particularly useful in interpreting the NIR sensor data. Any moisture sensor incorporated into the penetrometer of U.S. Pat. No. 10,337,159 would be exposed to heat from the nearby light source. This may result in reduced accuracy of both readings.

Therefore, there is a need for an in situ NIR sensing unit without an internal light source and an improved ability to sense constituents and other features of a media in which the NIR sensor is placed.

BRIEF SUMMARY OF THE INVENTION

One aspect of the invention according to this disclosure is an in situ NIR sensor or probe which may be inserted into a media and perform in situ NIR sensing. The probe includes various features within a housing such as a sensing element, comprising a light collecting fiber and a light emitting fiber, mounted opposite a mirror that is mounted at an angle to a transparent window which may be sapphire crystal.

The angle at which the mirror is mounted is beneficial for many reasons. First, it enables the use of near infrared light emitted by an external light source positioned up hole outside the probe. The light supplied by the external source is conveyed from the source into the probe housing by illuminating fibers in a fiber optic bundle. Media may be illuminated via reflection off the mirror and transmission through a transparent window such as a sapphire crystal. Second, the transmission of light to the media occurs while precluding supplied light reflected off the first and second surfaces of the sapphire window from reaching a light collecting fiber in the fiber bundle tip either directly or via further reflection off the mirror. Simultaneously, light reflected off the media may reach the tip of the light collecting fiber either directly or via further reflection off the mirror.

A second aspect of the invention, according to this disclosure, is a near infrared sensing unit comprising a tubular housing including a sidewall extending between a first end and a second end, and a transparent window formed in the sidewall of the housing. The sensing unit also comprises a sensing element mounted inside the housing. The sensing element configured to emit near infrared light and configured to collect near infrared light. The sensing unit also comprises mirror mounted inside the housing and opposite the sensing element. The mirror may be mounted at an angle with respect to the transparent window. The angle allows the mirror to reflect the near infrared light, emitted by the sensing element, through the transparent window. The sensing unit also comprises a conical tip connected to the first end of the housing, and the conical tip is configured to penetrate a media.

The sensing unit may also comprise the following features. A carriage disposed inside the tubular housing with the carriage abutting the side wall. A mirror mount formed in the carriage, and the mirror mount configured to hold the mirror at the angle with respect to the transparent window. Also, a sensor mount formed in the carriage, and the sensor mount configured to hold the sensing element opposite the mirror. Additionally, the carriage may be positioned inside the housing such that the mirror and sensing element are adjacent the transparent window.

The sensing unit may further comprise a light source external to the housing; and an optical fiber bundle connected to the sensing element and light source.

The angle of the mirror with respect to the transparent window may be in a range of 33.5 to 38.5 degrees.

The mirror may further comprise a mounting surface facing away from the transparent window, and a reflecting surface facing the transparent window. The transparent window may further comprise a first surface extending parallel to a second surface. A first plane may extend parallel and through the reflecting surface. A second plane may extend through the transparent window such that the second plane is parallel to the first and second surfaces. The angle may be defined by an intersection of the first plane and second plane, and the angle may be in a range of 33.5 to 38.5 degrees.

The sensing unit may further comprise a sapphire crystal forming the transparent window. The sapphire crystal may be configured to transmit near infrared light to the media on the exterior of the housing. The sapphire crystal may also be configured to transmit light reflected from the media into the housing.

The sensing unit may further comprise a central opening within the tubular housing. The central opening may be defined by the sidewall, and the central opening may extend between the first end and the second end. The sensing element and mirror may be mounted within the central opening adjacent the window.

The sensing element may further comprise at least one light emitting fiber and at least one light collecting fiber.

The sapphire crystal may include a first surface and a second surface. The first surface facing the interior of the housing, and the second surface facing the exterior of the housing. Also, the sensing element may be mounted in the housing such that the sensing element is configured to emit near infrared light in a path substantially parallel to a plane extending parallel to the first or second surfaces of the transparent window.

The sensing unit may further comprise an optical fiber bundle including a first bundle end comprising the sensing element and a second bundle end. Also, a spectrometer may be external to the housing, and the spectrometer may be connected to the second bundle end. The spectrometer may also be configured to determine variations between the near infrared light emitted by the sensing element and near infrared light detected by the sensing element. Additionally, a light source may be external to the housing, and the light source may be connected to the second bundle end. Also, the light source may be configured to transmit light to the sensing element through an optical fiber bundle.

The angle of the mirror with respect to the transparent window may allow the near infrared light to be transmitted through the sapphire crystal and precludes near infrared light reflected by the sapphire crystal from impinging on the sensing element either directly or via further reflection from the mirror.

A third aspect of the invention, according to this disclosure, includes a method of making a near infrared sensor. The method comprises various steps such as providing a housing including a first end, a sidewall extending between the first and second end, and a transparent window in the sidewall. Also, the method comprises mounting a sensing element inside the housing. The sensing element may be configured to emit near infrared light and detect near infrared light. Another step includes mounting a mirror inside the housing and opposite the sensing element such that the mirror is at an angle with respect to the transparent window and the angle allows the mirror to reflect the near infrared light, emitted by the sensing element, through the transparent window. A further step comprises connecting a conical tip to the first end of the housing, and the conical tip is configured to penetrate a media.

The method of making a near infrared sensor may further comprise the step of forming a carriage configured to be inserted into the housing. The carriage may include a mirror mount configured to hold the mirror at the angle with respect to the transparent window. The carriage may also include a sensor mount formed in the carriage. The sensor mount configured to hold the sensing element opposite the mirror. Another step may include placing the carriage into the housing such that the sensing element and mirror mounts are adjacent the transparent window.

The step of forming the carriage may further comprise forming the mirror mount such that the mirror mount is configured to hold the mirror at an angle with respect to the transparent window.

The step of providing a tubular housing may further comprise the step of using a sapphire crystal as the transparent window.

The step of mounting the mirror may further comprise the step of mounting the mirror at an angle with respect to the transparent window such that the angle of the mirror allows the near infrared light to be transmitted through the sapphire crystal and precludes near infrared light reflected by the sapphire crystal from impinging on the sensing element either directly or via further reflection from the mirror.

The step of mounting the mirror further comprises the step of mounting the mirror such the mirror is at an angle of 33.5 to 38.5 degrees with respect to the transparent window.

The step of mounting the sensing element further comprises the step of mounting the sensing element such that the sensing element is configured to emit near infrared light in a path that is substantially parallel to a plane extending through the transparent window and towards the first and second ends of the housing.

The method of making a near infrared sensor may further comprise the steps of providing a light source external to the housing; and connecting the light source to the sensing element with a fiber optic cable bundle. Also, the method may include providing a spectrometer external to the housing and connecting the spectrometer to the sensing element with the fiber optic cable.

BRIEF DESCRIPTION OF THE SEVERAL VIEWS OF THE DRAWINGS

The foregoing summary, as well as the detailed description of the preferred embodiments of the invention, will be better understood when read in conjunction with the appended drawings. For the purpose of illustrating the invention, there is shown in the drawings, which are diagrammatic, embodiments that are presently preferred. It should be understood, however, that the present invention is not limited to the precise arrangements and instrumentalities shown. In the drawings.

DETAILED DESCRIPTION OF THE INVENTION

Certain terminology is used in the following description for convenience only and is not limiting. The words "inner", "inwardly" and "outer", "outwardly" refer to directions toward and away from, respectively, a designated centerline or a geometric center of an element being described, the particular meaning being readily apparent from the context of the description. Also, as used herein, the words "connected" or "coupled" are each intended to include integrally formed members, direct connections between two distinct members without any other members interposed therebetween and indirect connections between members in which one or more other members are interposed therebetween. The terminology includes the words specifically mentioned above, derivatives thereof, and words of similar import.

Like numbers are used to indicate like elements throughout. Elements, components, and/or features that are discussed herein with reference to one or more of FIGS. 1-10 may be included in and/or utilized with any of FIGS. 1-10 without departing from the scope of the present disclosure. In general, elements that are likely to be included in a particular embodiment are illustrated in solid lines. Dashed lines may be utilized to indicate elements that are likely to be included but are within an element. Also, dashed lines are utilized to represent geometric elements.

FIGS. 1-10 provide examples, according to this disclosure, of an in situ NIR probe or sensing unit 1, method of making the in situ NIR probe 1 and the method of using the in situ NIR probe 1. The NIR probe 1 includes an NIR sensing element 110 and may perform in situ sensor readings allowing the NIR sensor readings to be taken at a field location. Additionally, the probe 1 may include other sensors such as soil force sensor 30 incorporated into sleeve 31 and more. More specifically, the NIR probe 1 is configured to be inserted into a media 150, such as soil and other geologic elements, and perform NIR spectrometry readings. The readings may be performed at various depths on the media 150 adjacent and/or surrounding the sensing element 110 as well as perform NIR sensor and soil force readings as the probe 1 is inserted into the media 150. This allows the soil force data to be obtained as the probe 1 is inserted and the NIR sensing to be performed on the same media 150.

It is noted that the NIR probe 1 may also perform sensing when a sample is positioned sufficiently near (i.e., inserted in a bore hole) the sensing element 110, and the probe 1 is not necessarily completely surrounded by a media 150.

Figure 5:
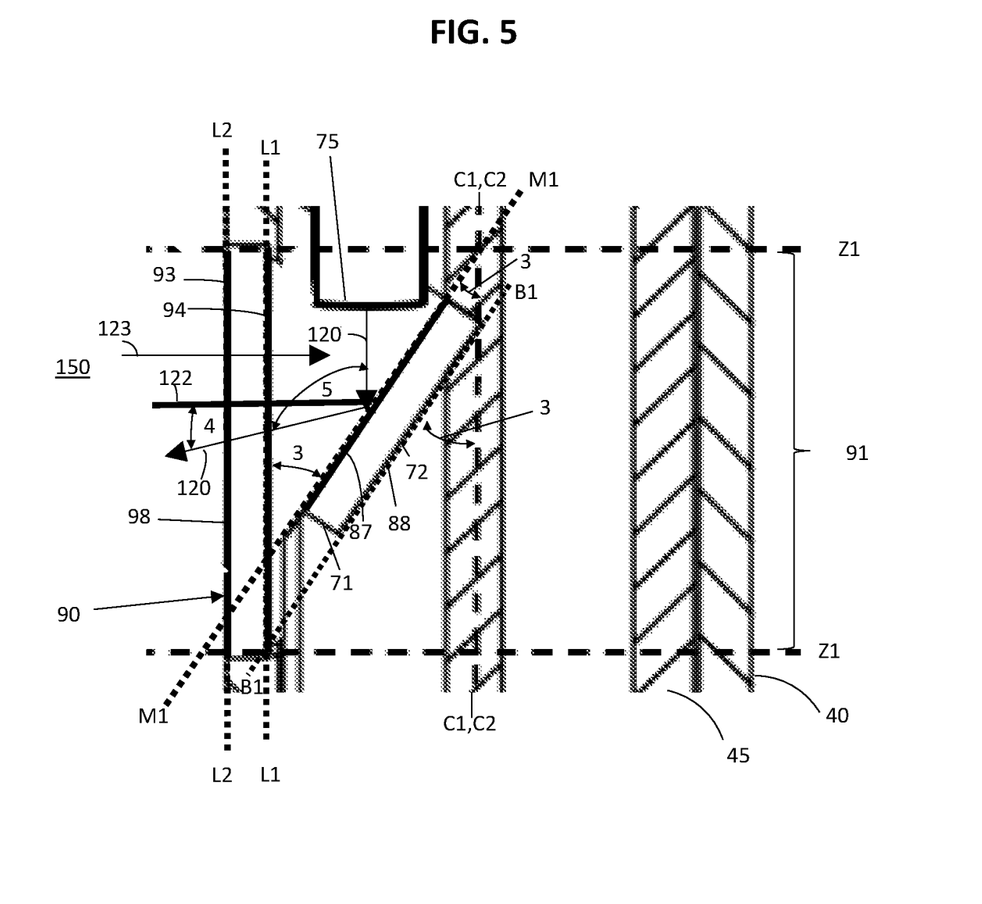
FIG. 5 is an exploded view of zone 91, as denoted by dashed line Z1, of the carriage of FIG. 3.
Figure 6:
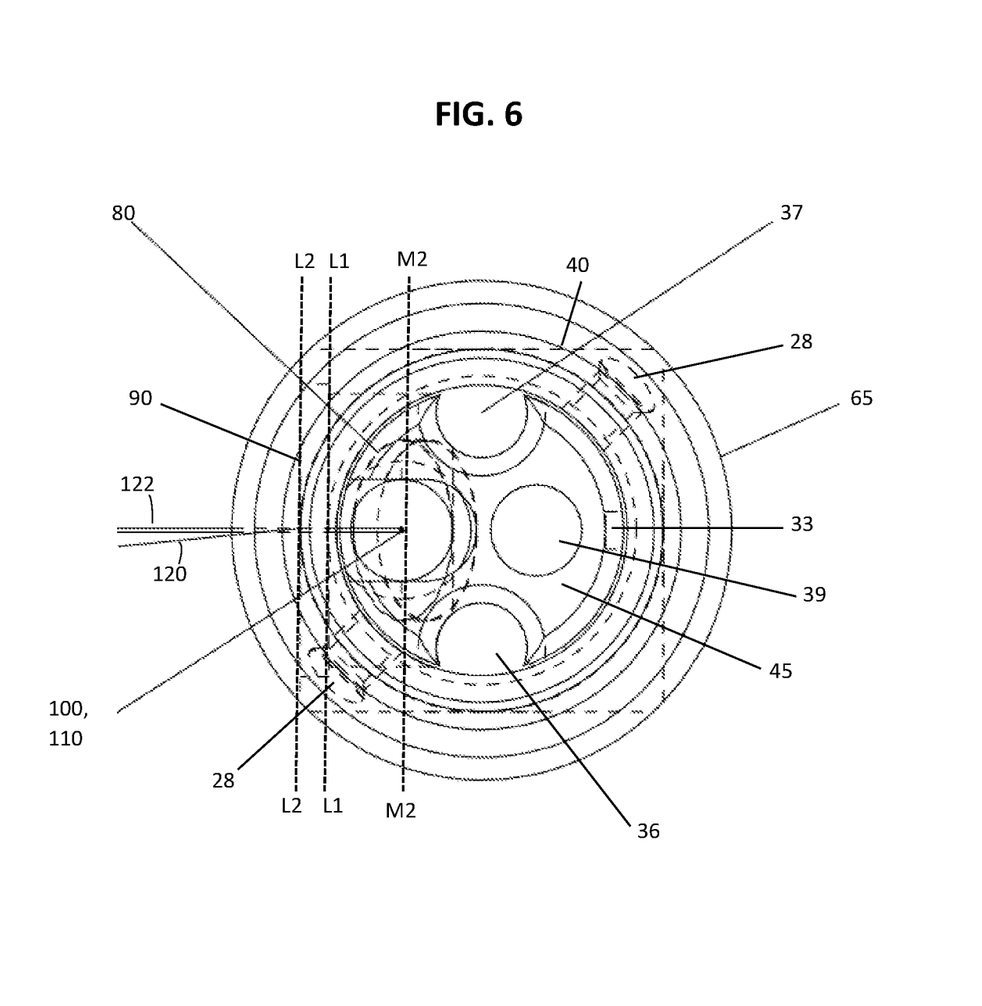
FIG. 6 is a top view of the embodiment of the NIR sensor probe of FIG. 1.
Figures 7, 8:
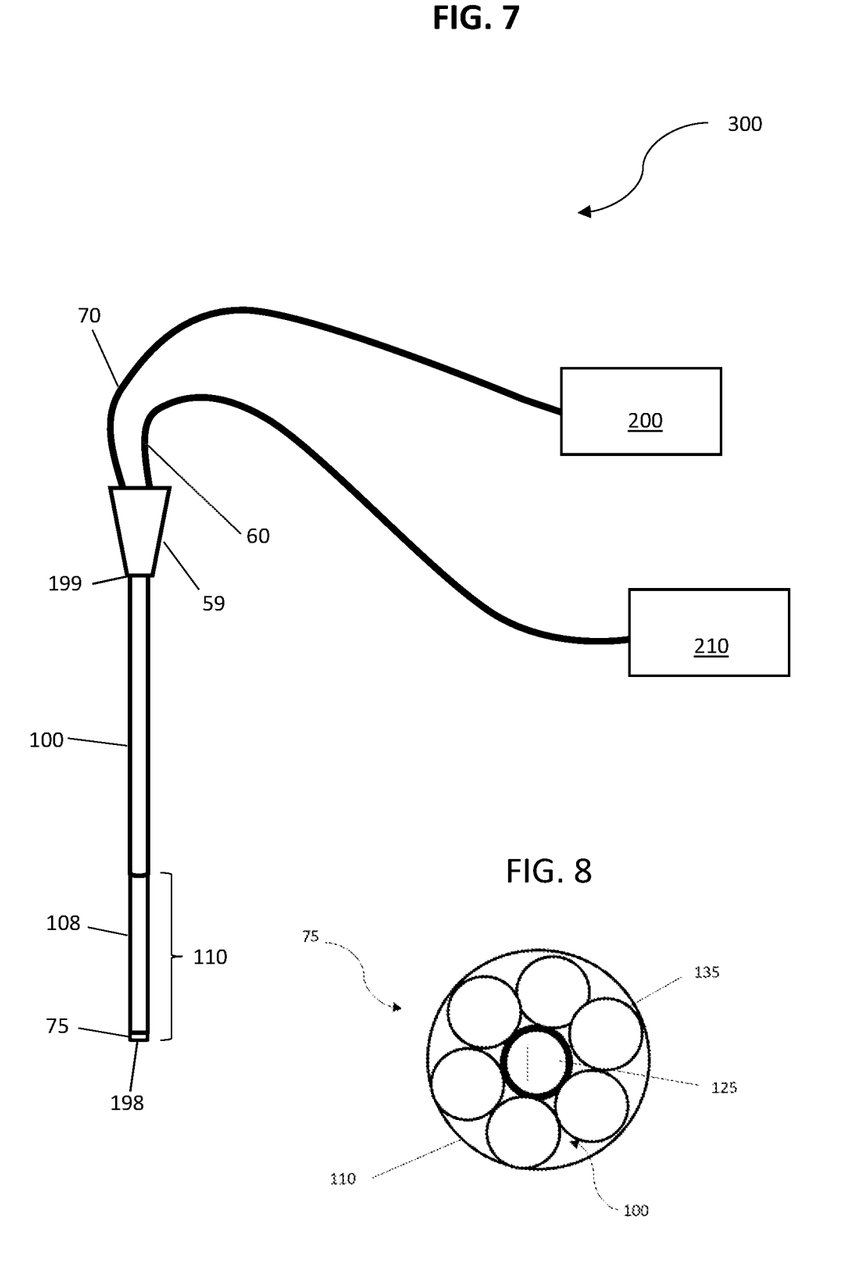
FIG. 7 depicts an embodiment of the NIR sensing system of the embodiment of the NIR sensing probe of FIG. 1.
FIG. 8 is a top view of an embodiment of the sensor tip of the NIR sensor in FIG. 7.

As shown in FIGS. 1-8, the NIR probe 1 includes a housing 65 with a window 90, a mirror 80, a fiber bundle 100 with a NIR sensing element 110 including sensing element tip 75, a spectrometer 200, a light source 210 and a bracket or carriage 45. The NIR sensing occurs within the housing 65 via NIR sensing element 110 and corresponding tip 75 which are part of an NIR system 300, as shown in FIG. 7, including a spectrometer 200 and light source 210 connected to the sensing element 110 by a fiber bundle 100 and separate fiber cables 70 and 60 pertaining to the spectrometer 200 and light source 210, respectively.

The housing 65 may include multiple in-line sections such as probe tip 15, sleeve 31, sensor housing 40, push rod 50, end cap 55. Sleeve 31, sensor housing 40, push rod 50, and end cap 55 are tubular and formed about a centerline C1. In this embodiment, the sensor housing section 40 has a rectangular or square tubular cross section and the other sections 31, 50, 55 include annular cross-sections. The tip 15 may be formed for ease of insertion into a media such as soil, wells, earth, etc. and may have various shapes and/or cross sections including conical, tapered, pointed, triangular, and the tip 15 may also be formed about centerline C1.

The sensor housing 40 is connected to the push rod 50 and the sleeve 31. One end of housing 65 is formed by the tip 15 which is connected to the sleeve 31. The other end of the housing is formed by the end cap 55 which is connected to the push rod 50. Sections 15, 31, 40, 50, 55 may be integrally formed or separate sections that are connected through suitable methods such as adhesives, opposable threaded fasteners, rivets, screws, epoxies, etc. Additionally, sections 15, 31, 40, 50, 55 may be formed of the same or similar materials that are resistant to deformation upon insertion into the media. For example, suitable materials may be three dimensionally stable materials including hard plastics, thermoplastics, metallic compounds or alloys (i.e., aluminum, stainless steel), ceramics, hard plastics, etc. Each section may be formed by a process corresponding to the chosen material such as metal milling, CNC machine, casting, ceramic molding, injection molding and additive manufacturing, etc.

The tip 15 abuts and is connected to the sleeve 31 by threaded fasteners or other methods as described above. Sleeve 31 may include a soil force sensor 30 and other types of sensors. The sleeve 31 may be connected to the sensor housing 40 via threaded or other fasteners 28, as shown in FIG. 6, inserted into through holes 42, as shown in FIG. 2) in the sensor housing 40.

Figure 2:
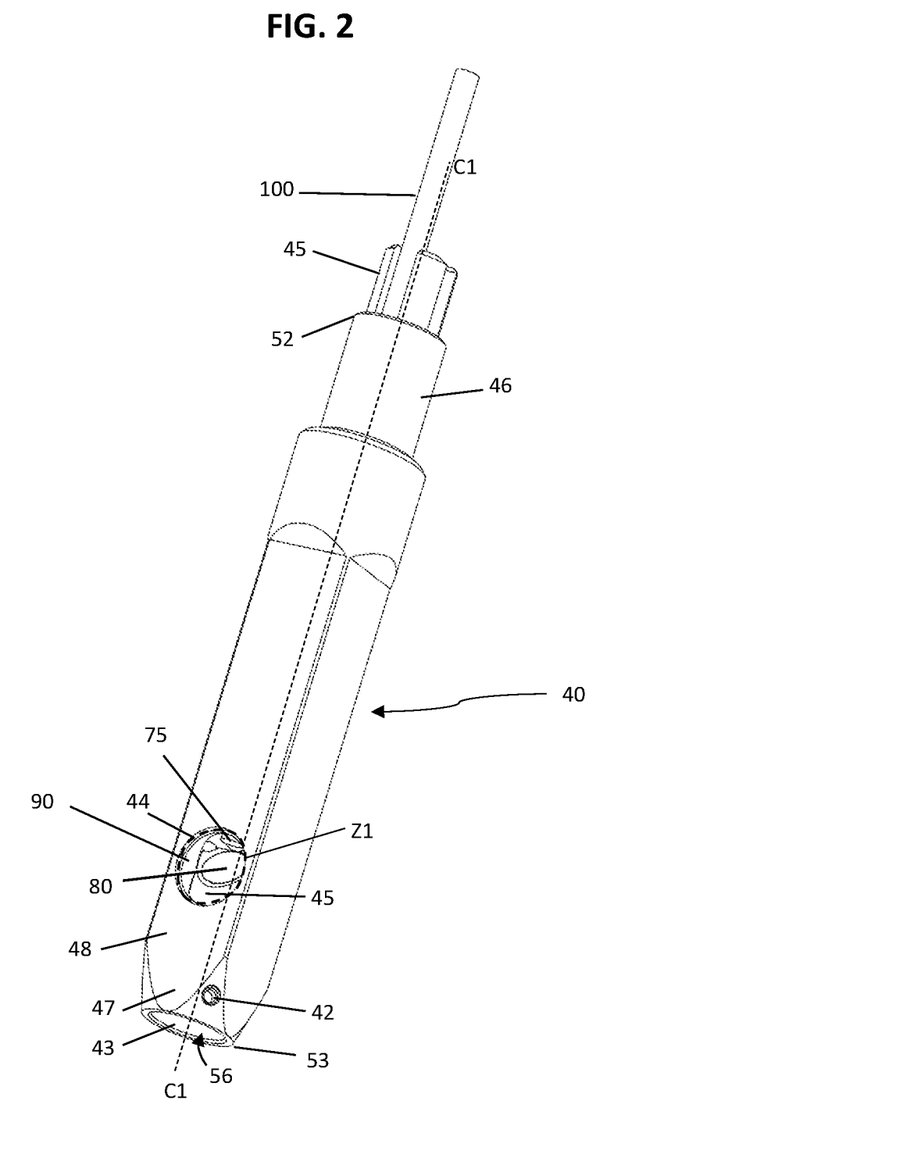
FIG. 2 is a front view of the NIR sensor housing of the embodiment of the NIR sensor probe of FIG. 1.
Figure 3:
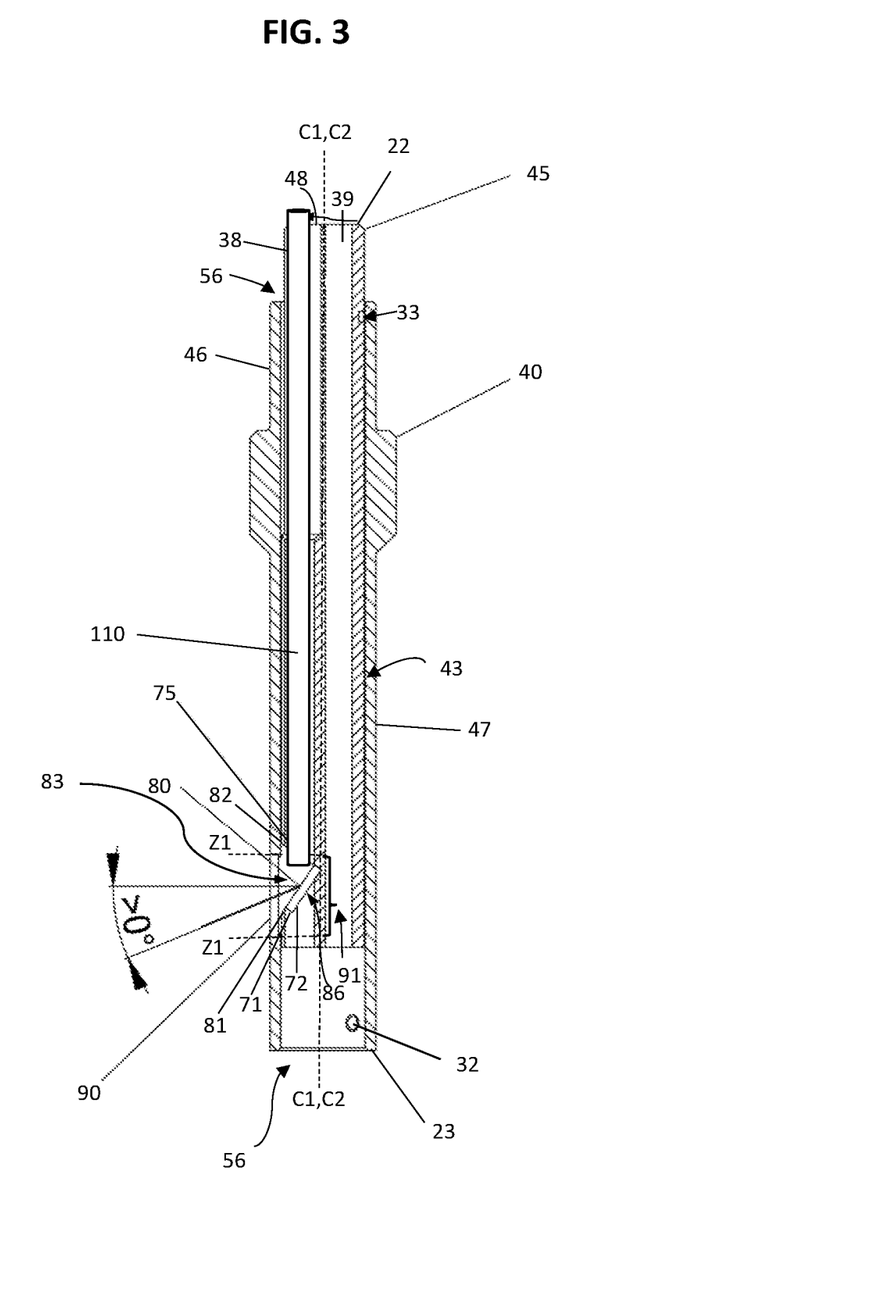
FIG. 3 is a longitudinal cross-sectional view of the NIR sensor housing of FIG. 2.

The sensor housing section 40 is shown in FIGS. 2-3 and comprises a tubular wall 48 having an exterior surface 47 and an interior surface 43 extending between a first end 52 and a second end 53. The interior surface 43 surrounds and defines a central opening 56 which also extends from the first end 52 to the second end 53. The first and second ends 52, 53 may be relatively smaller in diameter and/or width than a section of wall 48 therebetween. At the first end 52, sleeve section 46 is formed for insertion into the push rod 50. The second end 53 tapers for connection with the sleeve 31. Through hole 42 positioned on the second end 53 allows connection to the sleeve 31 with a fastener 28 such as a pin, ribbed fastener or threaded fastener. Additionally, the sleeve 46 and second end 53 may have features (not shown) such as threading and/or ridges for connection with the push rod 50 and sleeve 31.

An opening or aperture 44 extends through the housing wall 48 and the exterior and interior surfaces 47, 43, respectively. A transparent material, such as a sapphire crystal or other material with suitable light transmissivity in the NIR spectral range and hardness, fills the aperture 44 and serves as a transparent window 90 in the wall 48 between the sensing element tip 75 and external media 150. The sapphire crystal 90 may be secured in the aperture 44 by using a marine adhesive or other suitable elements including epoxies, adhesives and/or a bracket, etc.

The carriage 45 may be disposed within the sensor housing 40, as shown in FIG. 3, and the carriage 45 is configured to hold the NIR sensing element 110, mirror 80 as well as other sensors and cables. To permit sensing through window 90, the carriage 45 is secured in position such that the sensor tip 75 and mirror 80 are adjacent and directly opposite the window 90. More specifically, the mirror 80 and tip 75 may be within zone 91 which is denoted by dashed line Z1. The carriage may be secured to the housing 40 by inserting a set screw into securing hole 33, but other types of fasteners such as adhesives, epoxies, and/or hook and loop may be utilized.

Line Z1 surrounds the perimeter of window 90. Zone 91 extends within the boundaries of line Z1 surrounding the perimeter of the window surface 93 and into the housing 40 to the centerline C2. This zone 91 defines the three-dimensional zone in which the tip 75 and mirror 80 may be placed so the light 120 emitted from the sensor tip may be reflected by the mirror 80 to through the window to media 150.

It is noted in this case the window is annular or circular, but it is envisioned the window 90 may be other shapes including square or rectangular. If the window 90 has different shapes then line Z1 surround the perimeter of the window 90 and create a correspondingly shaped zone.

Figure 4:
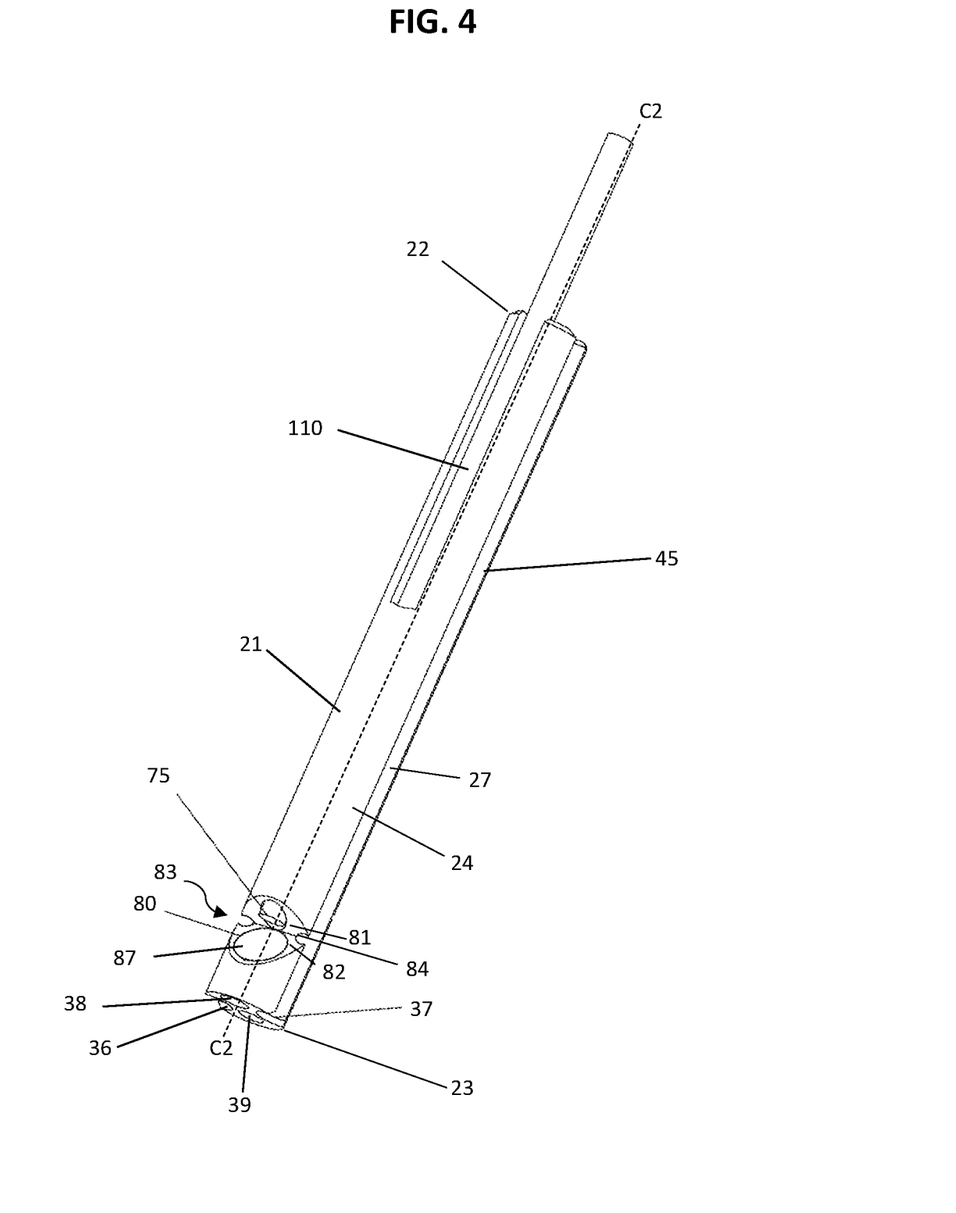
FIG. 4 is a front view of an embodiment of the carriage inside the NIR sensor housing of FIG. 2.

As shown in FIGS. 3 and 4, the carriage or bracket 45 has a centerline or central axis C2 which is coaxial and/or parallel to centerline C1 of the housing 40 and a body 21 with an exterior surface 24 extending between a first end 22 and a second end 23. Also, the carriage may include a mirror recess 83, securing hole 33, sensor wire channels 36, 37 and sensor mounts 38, 39. The first end 23 is positioned within the first end 53 of housing 40 and the second end 22 may extend beyond the first end 52 of housing 40. The exterior surface 24 may abut and be contiguous with the interior housing surface 43.

The carriage 45 may support several sensors. In this embodiment, the carriage includes sensor mounts 38 and 39 configured to hold sensors and/or sensing elements as well as wire channels 36 and 37 configured to hold sensor wiring. As shown, mount 39 is a through hole while channels 36 and 37, which also extend the length of the carriage 45, are defined by the external surface 24 with an opening 27 extending along the sides from the first end 23 to the second end 22 of the carriage 45. In this case, mount 38 holds the NIR sensing element 110 and channel 37 would hold any wiring (not shown) associated with a different sensor such as the soil force sensor 31. It is envisioned that holes 36, 37 and mounts 38, 39 may each hold a sensor/sensing element and/or allow wires to pass through the carriage 45. Additionally, it is envisioned that more or fewer mounts, including varying dimensions, may be formed in carriage 45.

Mount 38 is a modified through hole as it appears open on the carriage first end 22 and second end 23. However, the mirror recess 83, as shown in FIGS. 3-5, is formed in the mount 38, carriage body 21, and exterior surface 24. The recess 83 may be defined by a first surface 81 opposite and abutting a second surface 82 with the first and second surfaces 81, 82 extending outwardly and radially with respect to the centerline C2. Additionally, the first surface 81 may extend axially towards the first end 22 and the second surface 82 may extend axially towards the second end 23. As shown, surfaces 81 and 82 may abut and may be contiguous at joint 84.

A mount recess 86 may be formed in the carriage surface 82. The mount recess 86 is configured to hold the mirror 80 and may have an L shaped cross-section in surface 82 with a bottom surface 72 extending between surfaces 71 and 81. Like surface 82, bottom surface 72 extends radially and axially towards the second end 23. Additionally, the bottom surface 72 may extend entirely across the mount recess 76 or a portion of the mount recess 86. To ensure the mirror 80 is properly oriented towards the window 90, the bottom surface 72 is at an angle 3, as shown in FIG. 5 to centerline C2. Angle 3 extends between a plane B1 extending through and parallel to surface 72 and centerline C2. Due to the angle 3 of the bottom surface 72 on which the mirror 80 is mounted, a plane M1 extending through and parallel to mirror 80 is also positioned at the angle 3 to the centerline C2. The window 90 extends parallel to the centerline C2 so angle 3 also extends between plane M1 and planes L1 and L2 extending across and parallel to window surfaces 94 and 93, respectively.

The mirror 80 has a reflective surface 87 and mounting surface 88. The mirror surface 87 faces both the sensing element tip 75 and window 90. Mounting surface 88 faces surface 72 and away from the window 90. The mirror surface 87 and angle 3 allow the mirror 80 to reflect light emitted by sensing element tip 75 through the window 90 to media 150. The mirror 80 may be secured to surface 72 with a marine adhesive or other suitable elements including bonding agents (i.e., epoxies, adhesives) and/or fasteners.

A mirror 80 with a reflective surface 87 suitable for reflection of light in the NIR spectrum may be utilized. One example of a suitable mirror includes a protective gold mirror (e.g., sputtered or evaporated gold) coated with a thin protective dielectric film which may be a thin layer or multiple layers of a dielectric materials such as amorphous $SiO_2$ or $Si_3N_4$ (silicon nitride). This type of mirror 80 has a reflectivity of about >96% across the NIR spectral range.

FIG. 5 depicts an enlarged view of zone 91 which extends between lines Z1 and Z1. For ease of illustration, lines Z1 are shown extending through the carriage 45, but as stated above zone 91 is bounded by line Z1, the window first surface 94 and centerline C2. As shown, the mirror 80, sensing element tip 75 and window 90 are disposed in zone 91. Due to the mirror angle 3, the mirror 80 may reflect light 120 emitted from the sensing element tip 75 through the lens 90 to media 150. Light 122 reflected from media 150, then passes through window 90 and is sensed by NIR sensing element tip 75.

Light may be reflected from the sensing element tip 75, through the window 90, to the media, with the angle of the mirror 80 being in a relatively large range. However, in much of this range, light 120 passing through the window 90 may be reflected by the first surface 94 and/or second surface 93. These reflections may enter the sensor housing 40 and reach the sensing tip 75 impinging on the probes ability to detect the infrared light 123 reflected from the media 150 that passes through the window 90 to the sensing element tip 75. When this occurs, the reflected rays of light may cause inaccurate NIR sensing performed by the NIR sensing tip 75 and probe 1. As a result, the angle 3 of the mirror with respect to the lens 90 should be chosen from a range of angles 3 that preclude reflection of light 120 by first and second surfaces 94, 93 from striking the sensing tip 75.

To preclude light reflected by either the first of second surface 94, 93 from striking the sensing tip 75, the light 120 should be incident on the first surface at an angle 4 in a range of approximately 14-18 degrees or more optimally approximately 16 degrees from normal 122. With an angle of incidence 4, in the range of approximately 14-18 degrees, the angle of reflection may be sufficiently precluded with the angle of reflection being approximately zero. Within this range, an angle of incidence 4 of approximately 16 degrees is preferred and has an angle of reflection of zero or mostly closely to zero.

With an angle of incidence 4 in the range of approximately 14-18 degrees, the angle 5 between the light emitted from the sensing element and the light reflected by the mirror 80 is in an approximate range of 104-108 degrees, and more specifically 106 degrees.

To achieve the angle of incidence 4 in the range of 14-18 degrees, the mirror 80 should be mounted at angle 3 with a range of approximately 35-39 degrees between the plane M1 and L1, L2 and between plane M1 and centerline C2. To achieve the angle of incidence of approximately 16 degrees, angle 3 may be approximately 37 degrees. Therefore, mounting surface 72 within recess 86 may be formed such that it is at an angle 3 of approximately 35-38 degrees or preferably 37 degrees from the centerline C2 of the carriage 45.

When light 123 is reflected from media 150, the light 123 may be transmitted into the sensor housing 40 by window 90. Once inside the sensor housing 40, the light 123 may travel directly to the sensing tip 75. Additionally, the light 123 may reach the mirror 80 and be reflected. When the mirror 80 is mounted at angle 3 in the range of approximately 35-39 degrees, the angle provides the added benefit of directing light 123 towards the sensing tip 75.

FIG. 6 is a view into probe 1 from into the top of the pushrod 50. As shown, the fiber bundle 100 and NIR sensor 110 are within mount 38 of carriage 45. In this example, channels 36 and 37 are empty, but if the soil force sensor 30 or another sensor is present wires may be inserted in one of channels 36 or 37. Additionally, set securing hole 33 is shown for the connection of the carriage 45 to the housing 40, and fasteners 28 for attaching the housing 40 to sleeve 31 via through holes 42 are shown.

Further, the mirror 80 is laterally centered opposite the window 90 and is not rotated with respect to window 90. More specifically, a line M2 extending across the mirror surface 87 and contiguous with the mirror surface 87 is substantially parallel with planes L1 and L2.

FIGS. 7 and 8 depict an example, according to this disclosure, of an NIR sensing system 300 removed from the probe 1. As shown, the fiber bundle 100 may be an assembly including a protective cover surrounding a co-aligned arrangement of optical fibers capable of transmitting light in the near infrared spectral range. The fiber bundle 100 extends between a first bundle end 198 and a second bundle end 199. The first bundle end 198 includes tip 75 and sensing element 110. The fibers 125 and 135, which may be arranged as shown in the sensor tip 75 of FIG. 8, may include a single light collection fiber 125 surrounded by 6 illumination fibers 135. It is noted that the size and numbers of fibers 125 and 135 may vary. The fiber bundle 100 is surrounded by a tubular collar 108 which protects and binds fibers 125 and 135 together and assists in holding the tip in the proper position within the carriage 45. The tubular collar 108 may be formed of a material with suitable hardness and three-dimensional stability. Examples of a suitable material include aluminum, stainless steel, metallic alloys, hard plastics, ceramics, etc.

As shown in FIGS. 3 and 6, the sensing element 110 including tip 75 and tubular collar 108 is inserted into mount 38 of the carriage 45 and extends the length of the carriage 45. This length provides stability to the tip 75, but the collar 108 may be of varying lengths as long as the collar 108 maintains stability of the tip 75. Mount 38 holds sensing element 110 in a position which allows the illumination fibers 135 to emit light substantially parallel to the first and second surfaces 94, 93 of the window 90 and corresponding planes L1, L2 as well as centerlines C1, C2. Sensing element 110 may abut an interior surface 48 of the mount 38 and be held in place by various methods including a friction fit, epoxy, adhesives, fasteners, etc.

Figure 1:
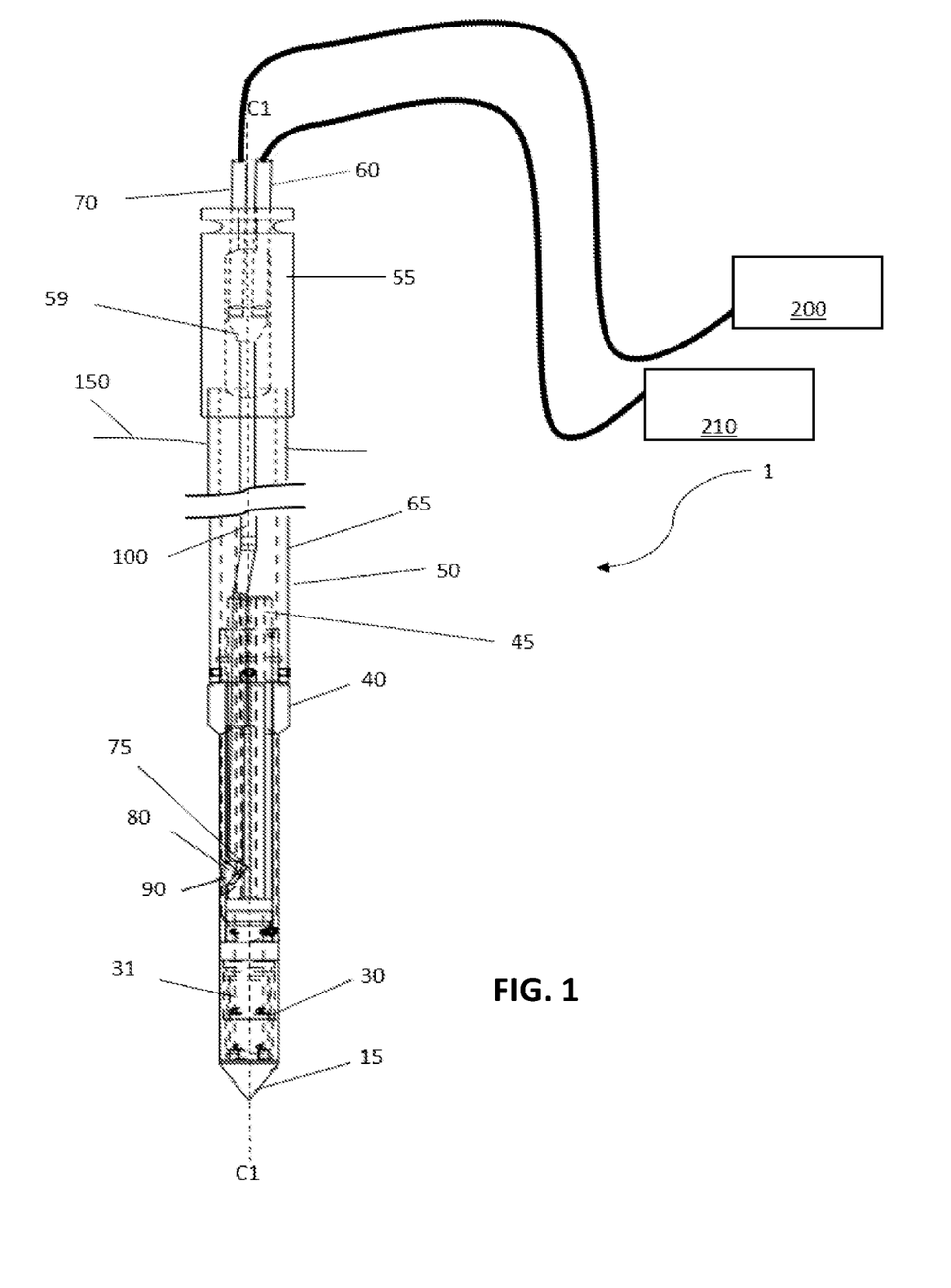
FIG. 1 is a side view of an embodiment of the NIR sensor probe according to this disclosure.

As shown in FIGS. 1 and 8, the fiber bundle 100 extends out of collar 108, carriage 45, and housing 40 through the push rod 50 into a fiber bundle divider 59 which may be disposed in the endcap 55. The fiber bundle divider 59 separates the illumination fibers 135 from the light collection fiber 125. The light illumination fibers 135 then form fiber bundle 60 which is connected to light source 210. The light sensing fiber 125 then forms fiber bundle 70 which is connected to the spectrometer 200. Both fiber bundles 60 and 70 are essentially fiber assemblies including optical fibers which are surrounded by a protective jacket.

The light source 210 and spectrometer 200 are both external to the probe 1 and connected to the sensing element 110 by fiber cables 60, 70 and 100. As is known in the art, the fiber bundle 100, light source 210 and spectrometer 200 may be selected to meet the goals of the NIR sensing.

Figure 9:
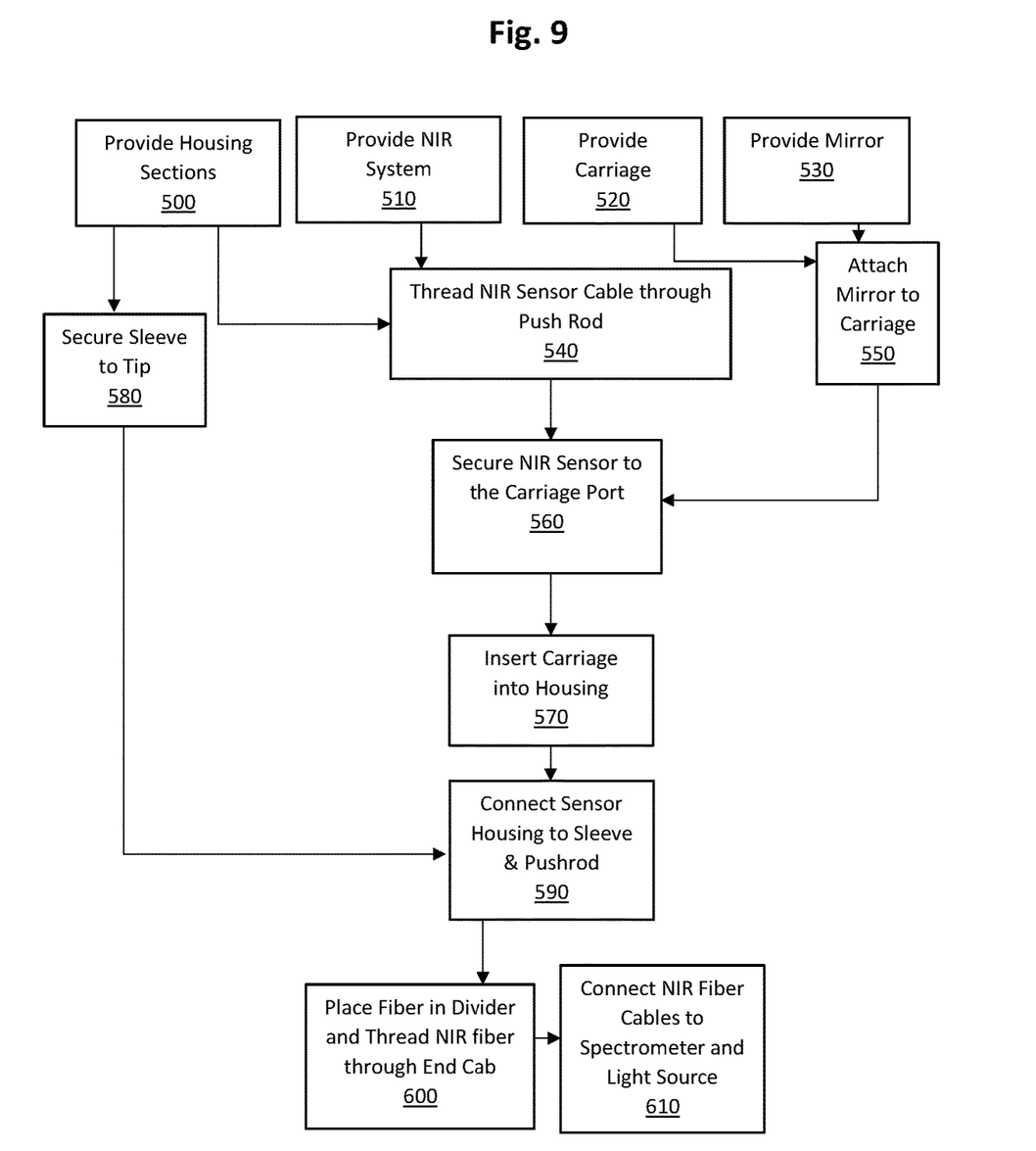
FIG. 9 is a schematic of an embodiment of a method of making the NIR sensor probe of FIG. 1.

FIG. 9 depicts an example of a method of making the NIR probe 1 according to this disclosure. Initially, in steps 500, 510, 520, and 530 different aspects of the NIR probe 1 are separately provided. In step 500, the housing 65 is provided. As described above, the housing 65 includes tip, 15, sleeve 31, sensor housing 40 including sapphire window 90, push rod section 50, and end cap 55. Each section 15, 31, 40, 50 and 55 are tubular, formed about a centerline C1, and formed so as to be connected to inline. Also, sensor housing 40 has a central opening 56 that is large enough to allow the carriage to slide through. Additionally, the length of the push rod 50 maybe altered to accommodate the depths at which NIR sensing may be desired. As discussed above, each part may be formed of dimensionally stable materials and as appropriate by processes such additive manufacturing, injection molding, casting, metal forming and milling, etc.

Separately, in step 510, the NIR system 300 is provided. As discussed above, this includes at least the sensing element 110 with sensing element tip 75 with collar 108, fiber bundle splitter 59, fiber bundles 60, 70 and 100 and an external light source 200 and spectrometer 210.

In step 520, the carriage 45, as described above, is provided. The carriage 45 is sized such that it may be inserted into central opening 56 in the sensor housing 40. Also, although the carriage 45 may have different mounts 38, 39 and channels 36, 37, for the example of the NIR probe 1 according to this disclosure, the carriage includes at least one mount 38 configured to receive the NIR sensing element 110. Recess 83 is also formed in the carriage 45 and includes a mounting recess 86 formed in mount 38. The mounting recess includes a bottom surface 72 at an angle 3 to the centerline. Angle 3 may be in the range of approximately 33.5 to 38.5 degrees and preferably is approximately 37.5 degrees.

The carriage 45 may be formed of dimensionally stable materials including hard plastics, metals, metallic compounds, ceramic, fiberglass, etc. Additionally, the carriage may be formed by suitable processes including additive manufacturing, injection molding, casting, metal forming and milling, etc.

In step 530, a mirror 80 such as a protective gold mirror, as described above, and sized appropriately for mounting on in the mirror recess 86 is provided.

Next, assembly of the probe 1 begins in three separate steps. In step 540, NIR sensor cable 100 including sensing element 110 may be threaded through the push rod 50. In step 550, the mirror 80 is securely attached, as described above, to the bottom surface 72 of mirror recess 56. Once attached, the mirror 80 is at approximately the same angle 3 as the bottom surface 72. Angle 3 is shown in FIG. 5 and discussed above as being approximately in the range of 33.5 to 37.5 degrees and more preferably approximately 37.5 degrees. In step 580, the sleeve 31 is attached to the tip 15 by any of the methods provided above.

In steps 560, the carriage 45 is further prepared for insertion into housing 40. The NIR sensing element 110, which was threaded through the push rod 50 in step 540, is threaded into mount 38 such that the sensing element tip 75 is directly opposite the mirror 80 and the tip 75 is able to emit light in a trajectory substantially parallel to the centerline C2 of the carriage. It is noted that the accuracy of the sensor readings may increase as the sensing element tip 75 is positioned closer to the mirror 80. As such the optimal position may include placing the tip 75 as close as possible to the mirror 80 without allowing the tip 75 to touch the mirror 80. The sensing element 110 is secured in the chosen position by methods described above.

In step 570, the carriage 45 with the NIR sensing element 110, and mirror 80 may be inserted or slid into the sensor housing 40 and secured in the proper position. As discussed above, the carriage 45 should be oriented so the mirror 80 and tip 75 are within zone 91 and directly opposite the window 90. Further, the mirror 80 should face the window 90 such that the line M2 which is contiguous with mirror surface 87 is substantially parallel to planes L1 and/or L2 of the window surfaces 94, 93, respectively. In other words, the mirror 80 should not be rotated with respect to the window. As discussed above, a set screw may be inserted into securing hole 33 and may be used to secure the carriage 45. The set screw offers the benefit of being able to remove the carriage 45 from to the sensor housing 40, but other suitable methods may also be used.

In step 590, sensor housing 40 is connected to additional elements of the housing. The housing second end 53 is connected to sleeve 31, which was connected to the tip 15 in step 580. This connection may be made using different connection element described above including fasteners 28 being inserted into through holes 42 in sensor housing 40. Additionally, the housing first end 52 is connected to the push rod 50, in which the fiber cable 100 was previously inserted.

In step 600, the end cap 55 is applied to the push rod 50. This is accomplished by threading fiber bundles 60 and 70 through the opening in the endcap 65. Next, the fiber bundle splitter 59 is attached to fiber bundles 60, 70 and 100 such that the fiber bundle 60 includes at least one light illumination fiber 135, fiber bundle 70 includes at least one light sensing fiber 125 and fiber bundle 100 includes at least one light illumination fiber 135 and at least one light sensing fiber 125. The end cap 55 is then slid over splitter 59 and the top of the push rod. Additionally, the end cap 55 may be secured to the push rod 55 by opposing threaded fasteners or other methods discussed above.

In step 610, the probe 1 is connected to the spectrometer 200 and light source 210. This connection is made by connecting fiber bundle 70 to spectrometer 200 and fiber bundle 60 to light source 210.

Figure 10:
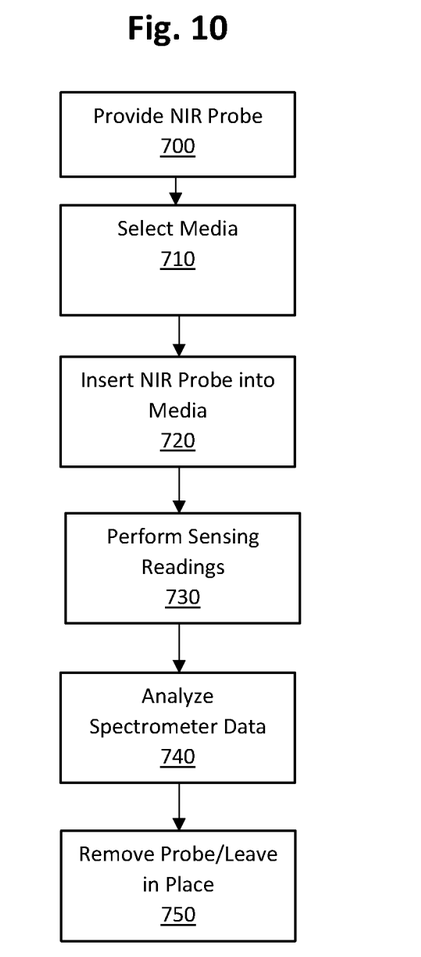
FIG. 10 is a schematic of an embodiment of using the NIR sensor probe of FIG. 1.

FIG. 10 provides an example of the steps involved in a method of using the NIR probe 1 according to this disclosure. Initially, in step 700, an NIR probe 1 as described in this disclosure is provided. Next, in step 710, the media 150 to be sampled is selected. The probe 1 may be used to sense characteristics of various types of media 150 including soil for agricultural and environmental studies, stored grain, compost, bore holes, etc.

In step 720, the probe 1 is inserted into the media 150. Depending on the condition of the media 150, this may involve insertion by hand, with the use of tools and/or machinery such as a hydraulic press.

In step 730, NIR sensing readings may be performed on the media 150 as the probe 1 is inserted and the probe reaches a depth where the window 90 is submerged or in contact with the media 150. In other words, the sensing may be performed at the desired depth of insertion and as the probe 1 reaches the depth.

To perform NIR sensing, the external light source 210 and spectrometer 200, which are both on the surface of the media 150, are activated. Light 120 is transmitted through fiber bundles 60 and 100 to the sensing element tip 75 and reflected by mirror 80. As discussed above, the mirror 80 is mounted on carriage 45 with an angle 3 of approximately 33.5 to 37.5 degrees between the mirror 80 and window 90. As a result, the mirror 80 may direct light 120 through the window with angle of incidence 4 on transparent window 90. Next, the light 123 reflected by the media 150 enters housing 40 through the window 90. Once in the housing 40, light 123 is sensed by the sensing element tip 75 and transmitted through fiber bundles 100 and 60 to the spectrometer 200 on the surface.

In step 740, the spectrometer 200 provides data corresponding the change in the transmitted light 120 and reflected light 123. This data is analyzed by methods known in the art to determine the characteristics of the sensed media 150.

In step 750, the probe 1 may be removed or left in place for on-going NIR sensing.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as generally defined in the appended claims.

The invention claimed is:

1. A near infrared sensing unit comprising:
   a tubular housing including a sidewall extending between a first end and a second end;
   a transparent window formed in the sidewall of the housing;
   a sensing element mounted inside the housing, the sensing element configured to emit near infrared light and configured to collect near infrared light;
   a mirror mounted inside the housing and opposite the sensing element, the mirror mounted at an angle with respect to the transparent window, the angle allowing the mirror to reflect the near infrared light, emitted by the sensing element, through the transparent window;
   a conical tip connected to the first end of the housing, the conical tip configured to penetrate a media; and
   a carriage disposed in the tubular housing, the carriage having an exterior surface abutting the sidewall;
   wherein the carriage includes a mirror recess formed in the exterior surface, the mirror recess defined by a first surface and a second surface, the second surface including a mount recess configured to hold the mirror at the angle with respect to the transparent window; and
   a sensor mount formed in the carriage, the sensor mount configured to hold the sensing element opposite the mirror;
   wherein the carriage is positioned inside the housing such that the mirror and sensing element are adjacent the transparent window.

2. The sensing unit of claim 1, further comprising:
   a light source external to the housing; and
   an optical fiber bundle connected to both the sensing element and the light source.

3. The sensing unit of claim 1, wherein the angle of the mirror with respect to the transparent window is in a range of 33.5 degrees to 38.5 degrees.

4. The sensing unit of claim 1, wherein the mirror further comprises:
   a mounting surface facing away from the transparent window; and
   a reflecting surface facing the transparent window,
   wherein the transparent window includes first and second parallel surfaces,
   wherein the angle is an angle of the reflecting surface relative to the first and second surfaces of the window, wherein the angle is in a range of 33.5 degrees to 38.5 degrees.

5. The sensing unit of claim 1,
   wherein the transparent window is sapphire crystal, the sapphire crystal configured to transmit near infrared light to the media exterior of the housing, and the sapphire crystal configured to transmit light reflected from the media into the housing.

6. The sensing unit of claim 5, wherein the angle of the mirror with respect to the transparent window allows the near infrared light to be transmitted through the sapphire crystal and precludes near infrared light reflected by the sapphire crystal from impinging on the sensing element either directly or via further reflection from the mirror.

7. The sensing unit of claim 1, further comprising:
   a central opening within the tubular housing, the central opening defined by the sidewall, and the central opening extending between the first end and the second end,
   wherein the sensing element and mirror are mounted within the central opening adjacent the window.

8. The sensing unit of claim 1, wherein the sensing element includes a fiber optic bundle that includes at least one light emitting fiber and at least one light collecting fiber.

9. The sensing unit of claim 1, wherein the window includes a first surface and a second surface, the first surface facing an interior of the housing, and the second surface substantially aligned with an exterior of the housing, and
   wherein the sensing element is mounted in the housing such that the sensing element is configured to emit near infrared light in a path substantially parallel to the first surface.

10. The sensing unit of claim 1,
    wherein the sensing element includes an optical fiber bundle that includes at least one light emitting fiber and at least one light collecting fiber, the optical fiber bundle having a first bundle end and a second bundle end; the sensing unit further comprising:
    a spectrometer external to the housing, the spectrometer connected to the at least one light collecting fiber at the second bundle end, the spectrometer configured to determine variations between the near infrared light emitted by the at least one light emitting fiber and near infrared light collected by the at least one light collecting fiber of the sensing element; and
    a light source external to the housing, the light source connected to the at least one light emitting fiber at the second bundle end, the light source configured to transmit light to the sensing element through the at least one light emitting fiber.

11. The sensing unit of claim 1, wherein the sensing element is configured to emit and collect near infrared light having a wavelength in a range from 800 nm to 2500 nm.

12. The sensing unit of claim 1, wherein the sensing element includes a fiber optic bundle that includes at least one light emitting fiber and at least one light collecting fiber that each have an end that defines a sensing element tip, wherein the sensing element tip is directly adjacent the mirror and emits the near infrared light towards the mirror and collects the near infrared light reflected from the mirror.

13. The sensing unit of claim 12, wherein the mirror is a flat mirror.

14. The sensing unit of claim 12, wherein the mirror and sensing element tip are laterally offset from a central longitudinal axis of the tubular housing and adjacent the transparent window.

15. The sensing unit of claim 12, wherein the window defines a space envelope that extends in a lateral direction across a width of the tubular housing and extends in an axial direction from a top edge of the window to a bottom edge of the window, wherein the sensing element tip and an entirety of the mirror are located within the space envelope.

16. The sensing unit of claim 1, wherein the angle is designed and configured to cause the near infrared light emitted by the sensing element to be reflected from the mirror and incident on a surface of the window at an acute angle with respect to an axis that is normal to the surface of the window, the acute angle designed and configured according to a wavelength of the near infrared light and a material type of the window to minimize a reflection of the near infrared light by the window while maximizing a transmission of the near infrared light through the window.

17. The sensing element of claim 16, wherein the wavelength of the near infrared light is in the range of 800 nm to 2500 nm, the material type is sapphire and the acute angle is in the range of 14 degrees to 18 degrees.

18. The sensing unit of claim 1, wherein the sensing element includes a fiber optic bundle that includes at least one light emitting fiber and at least one light collecting fiber, wherein the sensor mount is an elongate longitudinal opening in the carriage that intersects the mirror recess at the first surface, the fiber optic bundle disposed in the elongate longitudinal opening.

19. The sensing unit of claim 18, wherein an end of the sensing element protrudes from the first surface and is disposed in the mirror recess.

20. A near infrared sensing unit comprising:
    a tubular housing including a sidewall extending between a first end and a second end;
    a transparent window formed in the sidewall of the housing;
    a sensing element mounted inside the housing, the sensing element configured to emit near infrared light and configured to collect near infrared light;
    a mirror mounted inside the housing and opposite the sensing element, the mirror mounted at an angle with respect to the transparent window, the angle allowing the mirror to reflect the near infrared light, emitted by the sensing element, through the transparent window;
    a conical tip connected to the first end of the housing, the conical tip configured to penetrate a media; and
    a carriage disposed in the tubular housing, wherein the carriage includes a mirror recess defined by a first surface and a second surface, the second surface configured to hold the mirror at the angle with respect to the transparent window; and
    a sensor mount formed in the carriage, the sensor mount configured to hold the sensing element opposite the mirror, wherein an end of the sensing element protrudes from the first surface and is disposed in the mirror recess.

21. The sensing unit of claim 20, wherein the sensing element includes an optical fiber bundle that includes at least one light emitting fiber and at least one light collecting fiber, the sensing unit further comprising a light source external to the housing, the at least one light emitting fiber connected to the light source.

22. The sensing unit of claim 21, further comprising a spectrometer external to the housing, the spectrometer connected to the at least one light collecting fiber, the spectrometer configured to determine variations between the near infrared light emitted by the at least one light emitting fiber and near infrared light collected by the at least one light collecting fiber of the sensing element.

* * * * *